United States Patent [19]

Sauer et al.

[11] Patent Number: 5,049,492
[45] Date of Patent: Sep. 17, 1991

[54] BIOFILM MONITORING COUPON SYSTEM AND METHOD OF USE

[75] Inventors: Richard L. Sauer; David T. Flanagan, both of League City, Tex.

[73] Assignee: The United States of America as represented by the United States National Aeronautics and Space Administration, Washington, D.C.

[21] Appl. No.: 493,529

[22] Filed: Mar. 14, 1990

[51] Int. Cl.$^5$ .......................... G01N 1/16; G01N 1/18; G01N 1/20

[52] U.S. Cl. .................................. 435/30; 73/863.85; 73/863.86; 73/863.41; 73/863.22; 422/99; 422/101; 435/291; 435/292; 435/293

[58] Field of Search .................................. 436/39, 46; 73/863.85–863.86, 863.41, 863.22; 422/99, 101; 435/291, 30, 292, 293, 294

[56] References Cited

U.S. PATENT DOCUMENTS 4,631,961 12/1986 Yohe et al. .......................... 73/866.5

OTHER PUBLICATIONS

"Biological Fouling of Industrial Water Systems: A Problem Solving Approach," Marc W. Mittelman and Gill G. Geesey, Water Micro Associates, San Diego, Calif., 1987.

Primary Examiner—David L. Lacey
Assistant Examiner—David Redding
Attorney, Agent, or Firm—Russell E. Schlorff; Harold W. Adams; Edward K. Fein

[57] ABSTRACT

An apparatus and method for biofilm monitoring of a water distribution system which includes the mounting of at least one fitting 61 in a wall port 65 of a manifold 19 in the water distribution system with a passage 62 through the fitting in communication with the manifold flow stream and the insertion of a biofilm sampling member 77 through the fitting with planar sampling surfaces 91,92 of different surface treatment provided on linearly arrayed sample couplons of the sampling member disposed in the flow stream in edge-on parallel relation to the direction of the flow stream of the manifold under fluid-tight sealed conditions. The sampling member 77 is adapted to be aseptically removed from or inserted in the fitting and manifold under a positive pressure condition and the fitting passage 62 sealed immediately thereafter by appropriate closure device 60 so as to preclude contamination of the water distribution system through the fitting 61. The apparatus includes suitable structure 70 for clamping the sampling member 77 and for establishing electrical continuity between the sampling surfaces 91,92 and the system for minimizing electropotential effects. The apparatus may also include a plurality of fittings 61 and sampling members 77 mounted on the manifold 19 to permit extraction of the sampling members in a timed sequence throughout the monitoring period.

17 Claims, 2 Drawing Sheets

BIOFILM MONITORING COUPON SYSTEM AND METHOD OF USE

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

FIELD OF THE INVENTION

The invention relates to biofilm monitoring systems, and more particularly to a biofilm monitoring method and apparatus which permits the aseptic extraction and insertion of biofilm samples from a water distribution system with minimal risk of contaminating the system.

BACKGROUND ART

In almost all water distribution systems, the monitoring and maintenance of water quality is an important concern. All water systems, including the ultraclean water systems such as are used in the electronics industry, are prone to the formation of biofilms, which are films that result from the adhesion and subsequent proliferation of bacteria and other life forms on the internal walls and surfaces of such water systems. In almost all instances, such biofilms tend to degrade system performance, and in the case of potable water systems, can potentially result in serious adverse health effects in humans.

For long duration spaceflights and space missions associated with the deployment of space stations or the establishment of lunar and planetary bases, an assurance of potable and hygiene water systems is of a very high priority. For such long duration missions, the capability of recycling used waters to potable quality is a necessity. The ability to recycle water from humidity condensate wash water, or similar related sources, as is planned for long duration space missions, is presently based on generally unproven technology. Since water microbial quality requirements for such space missions are especially stringent, typically requiring a bacterial count of not more than 1 colony-forming unit per 100 ml of water, an ability to monitor the development of biofilms in the various water distribution systems so as to assist in maintenance of water quality has involved extensive research. Heretofore, biofilm monitoring methods and apparatus have almost always been associated with compromises of system sterility which cast doubt upon the validity of data acquired subsequent to extraction of biofilm samples.

Prior methods have included the provision of a tubular spool in the flow line of the distribution system wherein the internal cylindrical surface of the spool provides a sampling surface suitable for the accumulation and growth of biofilms thereon. At an appropriate time interval, the system is temporarily shut down and the spool removed therefrom to permit dissection of its biofilm sample surface into a plurality of samples by sawing, cutting or the like whereby a variety of biofilm analysis procedures may be applied to the individual sample pieces. The resultant heat which is generated in the dissection procedure and the likelihood of sample contamination are deterrents to accurate biofilm evaluation and monitoring procedures which typically involve microbe enumeration, microscopy examinations which may include epifluorescent microscopy and scanning electron microscopy examinations.

A published article entitled "BIOLOGICAL FOULING OF INDUSTRIAL WATER SYSTEMS A Problem Solving Approach" by Water Micro Associates of San Diego, California, 1987, discloses a "Robbins Biofilm Sampler" designed to provide replicate surfaces for studies of microbial attachment and subsequent biofilm formation. The surfaces are placed at various test locations in the system and after various periods of exposure are recovered from each test site. The potential for system contamination during the removal process is unacceptable for monitoring procedures where it is necessary to maintain a very high water quality. It is also not feasible or convenient to divide the sample surfaces into several portions to support different types of analyses. Further, the Robbins Biofilm Sampler does not provide a duel microbial barrier following coupon extraction.

SUMMARY OF THE INVENTION

The invention is a biofilm monitoring method and system which permits the aseptic extraction of biofilm samples from a water distribution system without contamination of the system and without requiring a system shutdown. The method and apparatus includes the mounting of at least one fitting in a wall port of a manifold in the water distribution system with a passage through the fitting in communication therewith. A biofilm sampling member having planar sampling surfaces provided on linearly arrayed sample coupons of the sampling member is inserted through its fitting with the sampling surface disposed edge-on to the flow stream of the manifold under fluid-tight sealed conditions. The sampling member is adapted to be aseptically removed from the fitting and manifold under positive pressure and the fitting passage sealed immediately thereafter by appropriate closure means so as to preclude contamination of the water distribution system through the fitting. The sample coupons are easily separable under aseptic conditions to permit individual evaluation of biofilm formations thereon. The apparatus includes means for establishing electrical continuity between the sampling surfaces to preclude the development of electropotentials between the sampling member and the piping system. The apparatus may also include a plurality of said fittings and sampling members so as to permit extraction of the sampling members in timed sequence throughout the monitoring period. In addition, insertion of additional samples can be accomplished by reversing the removal procedure described above.

DETAILED DESCRIPTION OF THE INVENTION

Figure 1:
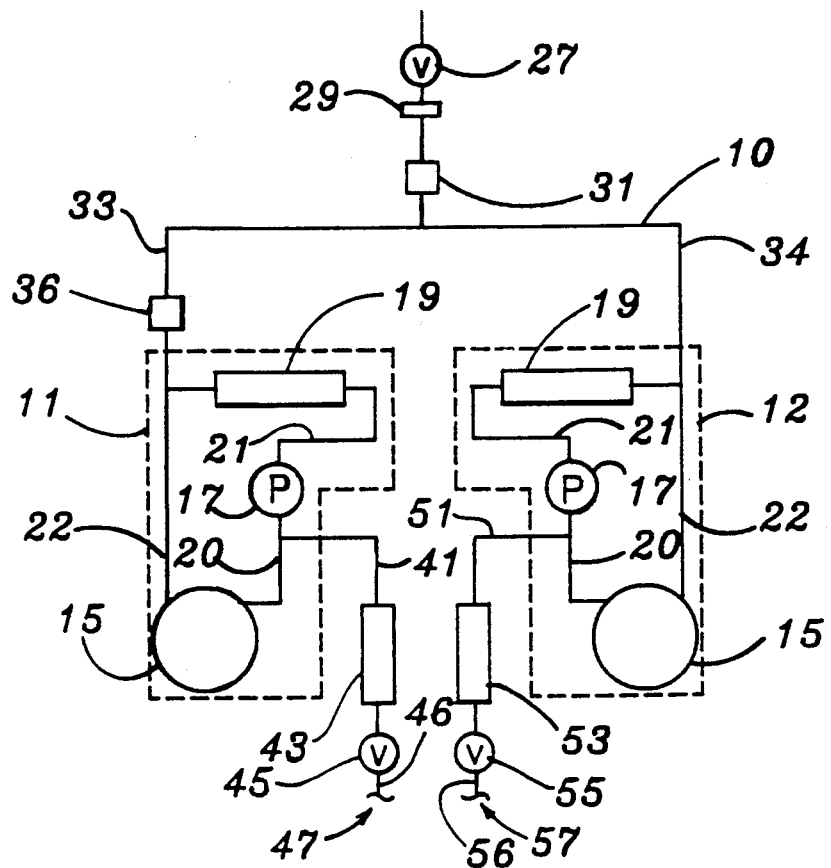
FIG. 1 is a schematic diagram of a test bed which includes two parallel water distribution subsystems, each of which simulates a spacecraft water system of a type which would support a long-duration flight.

Referring to FIG. 1 of the drawings there is shown a test bed 10 which was developed in a research program directed to biofilm monitoring and control. The test bed 10 is divided into two parallel subsystems 11, 12, each of which simulates a spacecraft water distribution system for supporting a long duration spaceflight. The present invention is directed to a biofilm monitoring method and apparatus which can be used to monitor and evaluate biofilm accumulation in water distribution systems, such as shown in FIG. 1, with minimal risk of system contamination and the compromise of system integrity.

Figure 2:
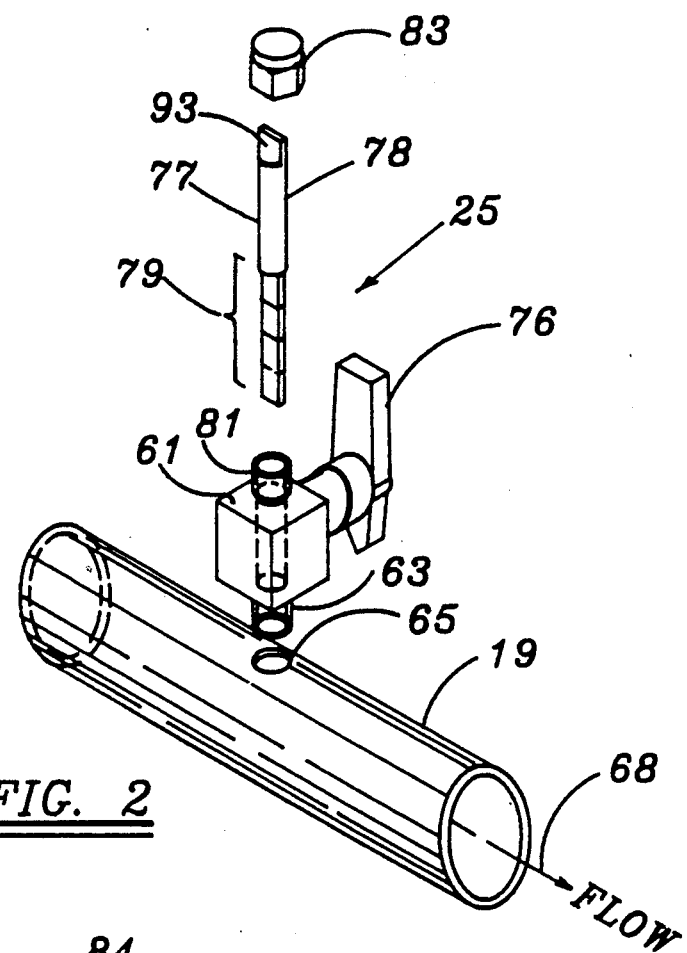
FIG. 2 is an exploded view in perspective of a biofilm sample coupon assembly adapted for installation in a sample manifold incorporated in a water distribution system to be monitored for biofilm accumulation and water quality.
Figure 4:
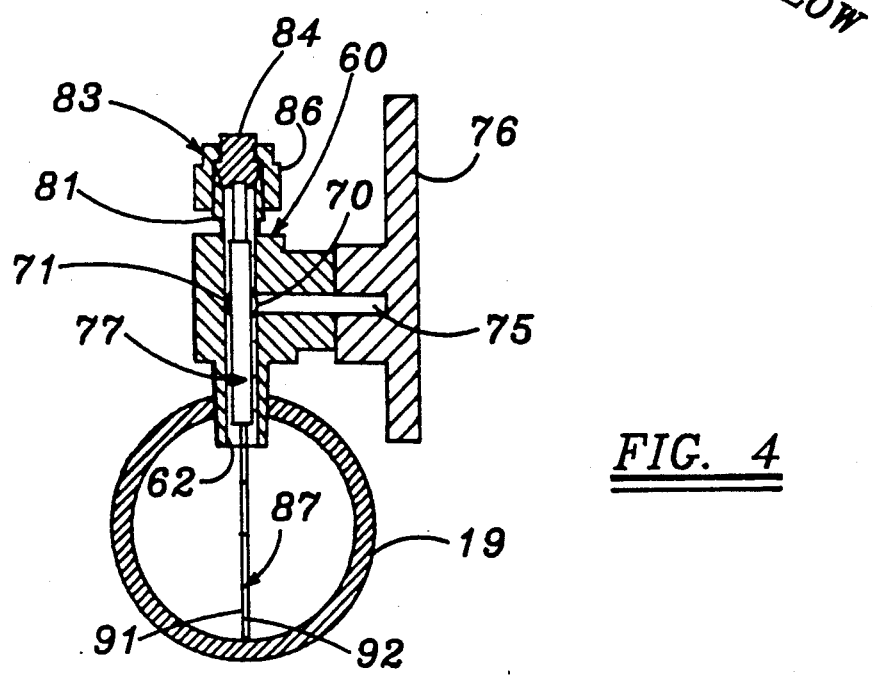
FIG. 4 is a view in cross section of the biofilm coupon sample assembly of FIG. 2, showing the assembly as mounted to a manifold of a water distribution system.

Each of the subsystems 11, 12 in the test bed 10 comprises a pump-driven recirculation loop which includes a 10-liter storage tank 15, a pump 17, a manifold 19 and connecting conduits 20, 21, 22 for establishing a distribution circuit. Each manifold 19 is adapted to receive a plurality of biofilm sampling assemblies 25 such as shown in detail in FIGS. 2 and 4. The test bed 10 with its two parallel subsystems 11, 12 is supplied with high quality make-up water from an appropriate water supply (not shown) by selective operation of a valve 27 installed in a conduit connecting thereto. When the valve 27 is opened, water is successively passed through a 0.22 $\mu$m microbial filter 29 and an ultraviolet disinfection device 31 immediately prior to entry into the test bed 10 through branch conduits 33, 34 which connect with the subsystems 11, 12 respectively.

The two parallel subsystems 11, 12 were provided in order to attain primary objectives of the research which were evaluation of iodine as an anti-microbial/anti-biofouling agent in such a system and the evaluation of biofilm formation in the system over a two year period. Accordingly, the subsystem 11 was iodinated at a level of about 2.5 mg/L by an iodinated ion-exchange resin contained in a microbial check valve 36 installed in the conduit 33. The other subsystem loop 12 had no iodine added.

In order to simulate actual use of a spacecraft water distribution system by a two-member crew, it was necessary to provide for 2-liter withdrawals of water from each of the subsystems every eight hours. Accordingly, a branch conduit 41 was tapped at one end into the conduit 20 of the subsystem 11. A manifold 43, similar to the manifolds 19 and adapted to receive biofilm sampling assemblies 25 therein was connected at its inlet end to the other end of the conduit 41. Water withdrawal from the subsystem 11 is controlled by a valve 45 in an outlet conduit 46 connected to the output end of the manifold 43 and providing an outlet port 47.

A similar branch conduit 51, sample manifold 53 with outlet conduit 56 connected thereto with control valve 55 and outlet port 57 was provided for the subsystem 12 to permit water withdrawals from the subsystem 12 in the same 2-liter amounts and eight hour frequency as were made from the subsystem 11.

To achieve the primary research objectives it was necessary to have an ability to collect biofilm samples aseptically to minimize or avoid the introduction of bacteria and other extraneous materials into the system and also avoid contamination of the sample during the process of removal from the system. The biofilm sampling assembly 25 of the invention, which was developed to meet these objectives, includes a quarter-turn ball valve 60 with a valve housing 61 having a flow passage 62 extending therethrough. The valve housing 61 includes an externally threaded end portion 63 coaxially formed about the flow passage 62 and adapted as a fitting for threaded connection in the internally threaded wall of a port 65 provided in a manifold, such as a manifold 19. The threaded portion 63 is preferably installed such that the longitudinal axis of the flow passage 62 is disposed in perpendicular relationship to the central axis 68 of the manifold 19 with which it communicates.

Mounted within the valve housing 61 is a ball valve element 70 in the form of a segment of a sphere with spherical sealing surfaces and an orifice 71 extending therethrough. The valve element 70 is connected at the end of a valve stem 75, the other end of which is provided with a handle 76. In conventional fashion, the valve element 70 is mounted for movement in the flow passage 62 between a first position in which the orifice 71 is aligned with the flow passage 62 and a second position in which the spherical sealing surfaces of the valve element are disposed to sealingly engage annular seats installed concentrically about the flow passage 62 and thereby close the passage 62.

Figure 3:
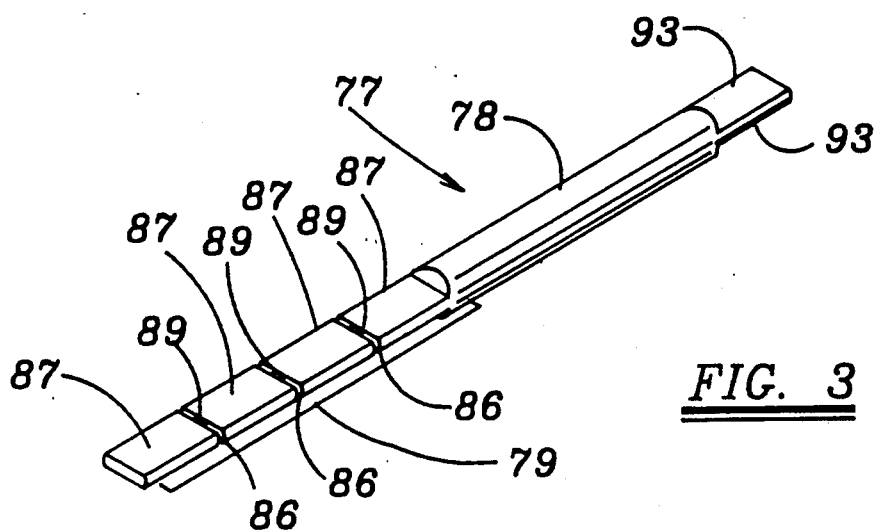
FIG. 3 is a perspective view of a biofilm sampling member which includes a biofilm sampling portion formed in segments to provide sample coupons.

The biofilm sampling assembly 25 also includes a biofilm sampling member 77, shown in detail in FIG. 3. The sampling member 77 includes a rod-like handle portion 78 and a biofilm sampling portion 79. The handle 78 is sized such that the biofilm sampling member can be inserted through the valve flow passage 62 and the orifice 71 of the valve element. The length of the handle 78 is such that the sampling member 77, when inserted in the valve housing 61, extends completely through the housing 61 with its biofilm sampling portion 79 extending into the flow stream of the manifold 19.

The valve housing 61 is also provided with an externally threaded boss 81 formed coaxially about the end of the flow passage 62 remote from the threaded end 63. The valve flow passage 62 extends through the boss 81 and is adapted to be sealed when the sampling member 77 is installed therein by means of a cap 83 which is threaded onto the boss 81. Preferably, the cap 83 contains only metallic material identical to that of which the valve housing 61 is constructed. It is particularly important that this material is the same as that which makes up the water distribution system to be monitored. Accordingly, the cap 83 is of the type which establishes a metal-to-metal seal with the valve housing 61, such as a SWAGELOK cap, a commercially available sealing member which includes an axially movable sealing member 84 having a frusto-conical seating surface which is adapted to seat on an internal frusto-conical seating surface provided in the boss 81 at the end of the flow passage 62 as the external member 86 of the cap 83 is threaded onto the boss 81.

It is to be understood that all the components of the biofilm sampling assembly 25 are sterilized and installed under aseptic conditions.

The biofilm sampling portion 79 of the sampling member 77 is integrally formed with the handle 78 and extends axially therefrom. The sampling portion 79 is in the form of a serrated blade having serrations 86 at equally spaced intervals along the length of the sampling portion 79 so as to divide the sampling portion 79 into segments or sample coupons 87 which are preferably of equal length and area. Each segment 87 is therefore integrally attached to the next adjacent segment 87 by a relatively thin and weak connecting link 89. Each segment 87 is formed with opposed planar sampling surfaces 91, 92, one of which is electro-polished and the other of which is a surface roughened by sanding. Other surface preparations can also be accommodated, e.g. TEFLON, paint, etc. Desirably the sampling member 77 is installed such that the sampling surfaces 91, 92 are disposed edge-on to the flow stream with all sampling surfaces similarly oriented into the flow stream and similarly situated with respect to the potential of biofilm adhesion and formation thereon.

As a means of achieving a selected orientation of the sampling surfaces 91, 92 with respect to the flow stream, the end of the handle 78 is formed with a pair of flat surfaces 93 formed parallel to one another and in parallel relation to the planar sample surfaces 91, 92. Prior to fastening the cap 83 to the valve housing 62, the parallel handle surfaces 93 may be aligned parallel with the longitudinal axis 68 of the manifold to insure an edge-on orientation of the sampling surfaces with the flow stream. The valve element 70 may then be turned a slight amount to clamplingly engage the handle 78 of the sampling member 77 and retain the edge-on orientation of the sampling surfaces in parallel relation to the direction of flow.

It is also to be noted, however, that the sampling member 77 is axially rotatable with the valve flow passage 62 and the orifice 71 of the valve element 70 such that the sampling surfaces 91, 92 may be oriented in face-on transverse relationship to the flow stream or at any other angular relationship with respect to the manifold axis 68 if such be desired. The ball valve element 70 can be used to clamp the handle of the sampling member 77 to accommodate any desired orientation of the sampling surfaces 91, 92. The valve element 70, however, also serves to establish electrical continuity between the sample coupons 87 and the metallic structure of the water distribution system such as to minimize any differences in electrical potentials which may occur with respect to the distribution system and the sampling segments.

The manifolds 19, 43 and 53 which are associated with the test bed 10 are each provided with a plurality of ports, such as the port 65, and each port is provided with a biofilm sampling assembly 25 mounted therein. The several biofilm sampling members 77 may therefore be extracted one at a time in sequence over extended time intervals sufficient to cover the monitoring period. Accordingly, the biofilm formation with respect to a water distribution system may be assessed and inducted at periodic time intervals.

In order to extract a sampling member 77 from a manifold it is required that the manifold be under a positive pressure condition, although the flow rate may be reduced if desired. By removal under the condition of positive pressure, water will well up and flow out of the valve flow passage 62 as a biofilm sampling member 77 is extracted therefrom. To reduce the amount of water lost from the system and to prevent contamination of the water system by possible entry of contaminants through the valve passage 62, it is necessary to close the valve 60 immediately after the sampling member 77 is withdrawn past the orifice of the valve element 70. A sterilized cap 83 is then replaced on the valve housing 61 to provide a dual barrier to possible contamination. Insertion of sampling members can be accomplished by reversing this procedure.

The formation of the biofilm sampling portion 79 in coupon segments permits an easy detachment and separation of the segments from one another by the application of sterilized vise grips or similar tools applied thereto without effecting the biofilm on planar surfaces 91.92. The sampling portion 79 can therefore be readily divided into multiple segments for accommodating multiple investigations and diverse biofilm evaluation procedures without the necessity of cutting or sawing through the sampling surfaces and the accompanying undesired generation of heat which can have an altering effect on the biofilms which could cast doubt on the validity of data obtained in post-extraction examination of the biofilms.

In the test bed 10, all of the components were manufactured from stainless steel and it has been found that the electro-polished sampling surfaces are less amenable to the formation of biofilm than the roughened surfaces. The iodinated system has also been observed to be successful in minimizing the presence of bacteria and its development whereas the non-iodinated subsystem was revealed to be contaminated in only three weeks of operation. After six months of testing, total organic carbon levels of 50 to 100 ppb were found in both subsystems with no significant corrosion of either subsystem. Average pH levels of 4.5 and 5.0 were found in the iodinated and non-iodinated subsystems, respectively. Traces of nitrate, sulfate and chloride were found in both subsystems but the phosphate level was below the limits of detection from which it may be inferred that phosphate is the growth-limiting nutrient for bacterial growth.

It will therefore be seen that a new improved method and apparatus for monitoring biofilm formation in a water distribution system is disclosed herein. The procedures for extraction of the biofilm sampling member under the condition of positive manifold pressure minimizes the risk of contaminating the system and the manner of dividing the biofilm sampling portion into easily detachable segments minimizes the risk of compromising the biofilm test data by the unwanted generation of heat and possible post-extraction contamination of the biofilms. The provision of means for establishing electrical continuity between the biofilm sampling coupons and the water distribution system reduces galvanic effects and minimizes the influence on biofilm formation and evaluation resulting therefrom. It is also to be noted that the monitoring apparatus of the invention includes a means for selective orientation of the sampling surfaces with respect to the flow stream to be monitored.

While the foregoing of the invention has been presented for purposes of description and explanation, it is to be understood that it is not intended to limit the invention to the precise form disclosed. For example, the sample surfaces need not be planar although the planar form is generally to be preferred. The ball valve might also be eliminated or replaced with some other means for closing off flow immediately following an extraction of a biofilm sampling member. It is to be appreciated therefore that various changes may be made by those skilled in the art without departing from the invention.

I claim:

1. A biofilm monitoring apparatus for use in a water distribution system having a manifold connected in the system so as to carry the water flow stream therethrough, said manifold having at least one opening in the wall thereof;

a valve means including a valve body having a passage therethrough and a valve element means mounted in said passage which is moveable between a first position in which said passage is open and a second position in which said passage is closed;

said valve element means having an orifice therethrough which is disposed in alignment with said valve passage when in the passage open position;

means for connecting said valve means to the manifold with said valve passage in fluid communication with the manifold through the manifold opening;

a biofilm sampling member of elongate form constructed so as to be asserted into the flow passage of the manifold through said valve body, said biofilm sampling member including a handle portion which is constructed so as to be slidably received through the orifice of he valve element means when in its passage open position and a sampling portion which extends into the manifold when the handle portion extends through the orifice of the valve element means wherein the sampling portion of the biofilm sampling member is of substantially flat blade-like configuration with a narrow peripheral edge and opposed planar surfaces suitable for biofilm accumulation and said biofilm sampling portion will be edge-on to the flow stream through the manifold when installed in the manifold;

means for removably connecting said biofilm sampling member to the valve body in fluid-tight sealed relationship therewith so that said biofilm sampling member is disposed int he valve passage with its sampling portion in the flow stream of the manifold whereby said elongate sampling member may be disconnected from the valve body and extracted from the manifold through the valve passage whenever it is desired to extract a biofilm sample from the manifold flow stream under positive pressure conditions of the water distribution system; and means for moving the valve element means to the valve passage closed position immediately following the removal of said biofilm sampling member past said valve element means orifice so as to preclude the contamination of the water distribution system through said valve passage.

2. A biofilm monitoring apparatus as set forth in claim 1 wherein the blade-like sampling portion of the biofilm sampling member is serrated at spaced intervals along its length to provide a plurality of sample coupons which can be easily and aseptically detached and separated from one another for individual analysis of their biofilm accumulations following an extraction of the biofilm sampling member from the manifold and said valve means.

3. A biofilm monitoring apparatus as set forth in claim 1 wherein said valve element means is constructed and arranged so as to move to a position whereby the valve element means clamps the biofilm sampling member with its sampling surfaces in a selected orientation with respect to the flow stream and establishes electrical continuity between said sampling portion and the water distribution system such that said sampling portion is deposed to experience the same electropotential effects as the rest of the distribution system.

4. A biofilm monitoring apparatus as set forth in claim 1 in combination with a manifold having a plurality of openings through the manifold wall and comprising a plurality of said valve means and at each of said openings, one of said valve means is connected to the manifold with its valve passage communicating with said manifold and said biofilm sampling member inserted therethrough.

5. A biofilm monitoring apparatus as set forth in claim 1 wherein at least one of said planar surfaces of said sampling member is electro-polished.

6. A biofilm monitoring apparatus as set forth in claim 1 wherein one of said planar surfaces of said sampling member is electro-polished and the other of said planar surfaces is a roughened sanded surface.

7. The combination as set forth in claim 4 wherein said biofilm monitoring apparatus is fabricated from the same material as said manifold.

8. A biofilm monitoring apparatus in combination with a water distribution system which includes a manifold connected therein to carry the flow stream of said system, said manifold having at least one port provided in the wall thereof;

fitting means connected in said port of said manifold, said fitting means having a passage extending therethrough in fluid communication with said manifold;

at least one elongate biofilm sampling member sized for insertion into said passage comprising a handle portion and a sampling portion each with surfaces constructed and positioned so as to be suitable for the formation and growth of biofilm thereon, wherein the sampling portion of the biofilm sampling member is of flat blade-like configuration with a narrow peripheral edge and opposed planar surfaces suitable for biofilm accumulation and said biofilm sampling portion is installed edge-on to the flow stream through the manifold;

means for removably connecting said biofilm sampling member to said fitting means in fluid-tight sealed relationship therewith so that said biofilm sampling member is disposed in said fitting with its sampling portion in the flow stream of the manifold whereby said elongate sampling member may be disconnected from the fitting and extracted from said manifold and fitting means whenever it is desired to extract a biofilm sample from the flow stream under a positive pressure condition of said flow stream; and means for closing said fitting passage immediately following the extraction of said biofilm sampling members so as to preclude contamination of said water distribution system through said fitting passage.

9. The combination as set forth in claim 8 wherein the blade-like sampling portion of the biofilm sampling member is serrated at spaced intervals along its length to provide a plurality of sample coupons which can be easily and aseptically detached and separated from one another for individual analysis of their biofilm accumulations following an extraction of the biofilm sampling member from said manifold and said fitting means.

10. The combination as set forth in claim 8 further comprising means for establishing electrical continuity between said biofilm sampling portion and the water distribution system.

11. The combination as set forth in claim 9 wherein said manifold is provided with a plurality of ports int he wall thereof, comprising a plurality of said fitting means and at least one said sampling member comprises a plurality of said sampling members, each one of said ports are constructed and arranged so as to provide connection to one of said fitting means and one of said biofilm sampling members.

12. A method of biofilm sampling of a water distribution system which includes a manifold mounted to carry the flow stream of the system, said method comprising the steps of mounting a fitting means having a passage therethrough to said manifold with its passage in communication with said manifold;

inserting a biofilm sampling member to extend through said passage into the flow stream in said manifold wherein said sampling member comprises sampling surfaces constructed and arranged so as to provide for the formation and adhesion of biofilm thereon wherein the sampling member is provided with replicate planar sampling surfaces disposed edge wise to the flow stream when the sampling member is extended therein;

sealing said passage when the sampling member is inserted to extend therethrough; and after a predetermined time interval unsealing said passage and aseptically extracting the sampling member from the manifold flow stream and passage under a positive pressure condition of the flow stream so that evaluation analysis may be made of biofilm on said sampling surfaces which may have formed during said time interval.

13. A method of biofilm sampling as set forth in claim 12 including the step of closing said passage immediately after extraction of the sampling member to preclude entry of contaminants into the water distribution system.

14. A method of biofilm sampling as set forth in claim 12 which includes the step of establishing electrical continuity between the biofilm sampling member and the water distribution system such that differential electropotentials of said water distribution system and biofilm sampling member are eliminated.

15. A method of biofilm sampling as set forth in claim 14 wherein said sampling member includes a plurality of sample coupon elements disposed in linear array, each one of said sample coupon elements having opposed sampling surfaces, one of which is an electro-polished surface and the other is a roughened surface.

16. A method of biofilm sampling as set forth in claim 12 wherein said manifold comprises a second fitting means having a passage therethrough and in communication with said manifold and wherein said method further comprises the step of inserting a second biofilm sampling member to extend through said passage into the flow stream in said manifold wherein said sampling member includes sampling surfaces suitable for the formation and adhesion of biofilm which are disposed in said flow stream.

17. A method of biofilm sampling as set forth in claim 12 wherein a plurality of said biofilm sampling members, each having biofilm sampling surfaces, are removably mounted on the manifold with their sampling surfaces disposed in the flow stream of the manifold under fluid-tight sealed conditions, said method including the step of aseptically and sequentially extracting each of said biofilm sampling members under a positive pressure condition of the manifold, each said extraction occurring at successively greater time intervals throughout the desired monitoring period.

* * * * *